US010131764B2

(12) United States Patent
Naert et al.

(10) Patent No.: US 10,131,764 B2
(45) Date of Patent: Nov. 20, 2018

(54) PLASTICIZERS PRODUCTION AND USE (71) Applicant: ExxonMobil Chemical Patents Inc., Baytown, TX (US)

(72) Inventors: Didier A. Naert, Brussels (BE); Bernard F. Leroy, C'eroux-Mousty (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 8 days.

(21) Appl. No.: 15/404,586

(22) Filed: Jan. 12, 2017

(65) Prior Publication Data

US 2017/0253723 A1  Sep. 7, 2017

Related U.S. Application Data

(60) Provisional application No. 62/304,718, filed on Mar. 7, 2016.

(51) Int. Cl.
| *C08K 5/101* | (2006.01) |
| *C07C 69/76* | (2006.01) |
| *C07C 67/08* | (2006.01) |
| *C07C 51/16* | (2006.01) |
| *C07C 2/64* | (2006.01) |
| *C07C 2/74* | (2006.01) |
| *C07C 2/84* | (2006.01) |
| *C07C 2/86* | (2006.01) |
| *C07C 5/367* | (2006.01) |

(52) U.S. Cl.
CPC ............... *C08K 5/101* (2013.01); *C07C 2/74* (2013.01); *C07C 2/84* (2013.01); *C07C 2/864* (2013.01); *C07C 5/367* (2013.01); *C07C 69/76* (2013.01); *C07C 2601/14* (2017.05)

(58) Field of Classification Search
CPC .......... C08K 5/101; C07C 2/64; C07C 51/16; C07C 67/08; C07C 69/76
USPC ........................................................ 524/299
See application file for complete search history.

(56) References Cited

U.S. PATENT DOCUMENTS

| 6,437,170 | B1 | 8/2002 | Thil et al. |
| 7,786,201 | B2 | 8/2010 | Grass et al. |
| 8,329,796 | B2 | 12/2012 | Grass |
| 8,829,093 | B2 * | 9/2014 | Dakka ............ C08K 5/12 524/284 |
| 9,321,898 | B2 | 4/2016 | Dakka et al. |
| 2014/0315021 | A1 | 10/2014 | Naert et al. |
| 2015/0140350 | A1 | 5/2015 | Dakka et al. |

FOREIGN PATENT DOCUMENTS

WO   WO2014-117076   7/2014

OTHER PUBLICATIONS

U.S. Appl. No. 62/304,727, filed Mar. 7, 2016, Naert et al.
Godwin, A.D., et al., "*Plasticizers*," Applied Polymer Science: 21$^{st}$ Century, Elsevier, 2000, pp. 157-175.

* cited by examiner

*Primary Examiner* — Ling Siu Choi
*Assistant Examiner* — Ronald Grinsted (57) ABSTRACT

This disclosure relates to aromatic ester plasticizers, including methyl biphenyl carboxylic acid esters of alcohols having an average carbon number ranging from 9.0 to 9.4 and a degree of branching of 3.0 or less, preferably 2.2 or less, to mixtures of such plasticizers, to compositions comprising the plasticizers and to thermoplastic polymer, such as polyvinylchloride, that contains the plasticizers.

5 Claims, 2 Drawing Sheets

PLASTICIZERS PRODUCTION AND USE

CROSS REFERENCE TO RELATED APPLICATIONS

This invention claims priority to and the benefit of U.S. Ser. No. 62/304,718, filed Mar. 7, 2016, and relates to U.S. Ser. No. 62/304,727, filed Mar. 7, 2016, and is also related to U.S. Ser. No. 14/516,239, filed Oct. 16, 2014.

FIELD OF THE INVENTION

This disclosure relates to aromatic ester plasticizers, to compositions comprising the plasticizers and to thermoplastic polymer, such as polyvinylchloride, containing the same.

BACKGROUND OF THE INVENTION

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, silyl-terminated polyethers, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Commonly assigned US 2015/0140350 identified plasticized vinyl chloride formulations using methyl biphenyl carboxylic acid esters. Suitable esters are methyl biphenyl carboxylate of $C_4$ to $C_{14}$ oxo alcohols. Commonly assigned US 2014/0315021 identified various blends of commercially available plasticizers with methyl biphenyl carboxylate esters.

Methyl biphenyl carboxylate ester plasticizers having improved properties such as lower viscosity and improved gelation are desired. Such plasticizers would be useful in PVC plastisols.

SUMMARY OF THE INVENTION

The present invention relates, in part, to the discovery that methyl biphenyl carboxylic acid esters formed from alcohol mixtures with an average carbon number ("ACN") ranging from 9.0-9.4 and a degree branching of 3.0 or less, preferably 2.2 or less, e.g., 2.0 or less, are especially good plasticizers. These mixtures exhibit lower volatility, lower viscosity and superior gelation and fusion properties when utilized as polymer plasticizer.

Accordingly, in one aspect, the present invention relates to a mixture, comprising one or more methyl biphenyl carboxylic acid esters corresponding to the following formula:

where R is an alkyl residue of an alcohol having a degree of branching ranging from 0.0 to 3.0, preferably from 0.0 to 2.2, e.g., from 0.0 to 2.0, and an ACN ranging from 9.0 to 9.4 Suitable alcohols for making such esters have a carbon number ranging from 8 to 11 ($C_8$ to $C_{11}$).

In another aspect, the present invention relates to a polymer composition comprising a thermoplastic polymer and at least one plasticizer mixture of one or more methyl biphenyl carboxylic acid esters of the following formula:

wherein R is an alkyl residue of an alcohol having a degree of branching ranging from 0.0 to 3.0, preferably from 0.0 to 2.2, e.g., from 0.0 to 2.0, and a ACN ranging from 9.0 to 9.4. Again, suitable alcohols for making such esters have a carbon number ranging from 8 to 11 ($C_8$ to $C_{11}$).

Yet another aspect of the invention relates to a process for making a mixture of methyl biphenyl carboxylic acid esters of the following formula:

wherein R is an alkyl residual of an alcohol having a degree of branching ranging from 0.0 to 3.0, preferably from 0.0 to 2.2, e.g., from 0.0 to 2.0, and an ACN ranging from 9.0 to 9.4, comprising a number of steps. The first step is reacting benzene or alkylated benzene under conditions appropriate to form alkylated biphenyl or optionally alkylating biphenyl to form said alkylated biphenyl. The second step is oxidizing the alkyl group on said alkylated biphenyl to form one carboxylic acid group. The third step is reacting said carboxylic acid group with alcohols comprising alcohols having a degree of branching ranging from 0.0 to 3.0, preferably from 0.0 to 2.2, e.g., from 0.0 to 2.0, and an average carbon number ranging from 9.0 to 9.4 under esterification conditions sufficient to form said mixture.

It has further been observed that methyl biphenyl carboxylic acid ester isomers having the methyl and carboxylic acid ester substituents closer to the para positions have lower viscosity than other isomers of the same ester. Accordingly, preferred methyl biphenyl carboxylic acid ester(s) are para-para (4'-4), meta-para (3'-4), para-meta (4'-3), and meta-meta (3'-3) isomers. The viscosity of the inventive methyl biphenyl carboxylic acid ester blends can be tailored by increasing or decreasing the concentration of isomers having substituents in the para-para, meta-para, para-meta, and/or meta-meta positions.

DETAILED DESCRIPTION OF THE INVENTION

All numerical values within the detailed description and the claims herein are modified by "about" or "approximately" to the extent necessary to account for experimental error and variations that would be expected by a person having ordinary skill in the art. Unless otherwise indicated, room temperature is about 23° C.

It has been discovered that mixtures of one or more methyl biphenyl carboxylic acid esters of alcohols having a degree of branching ranging from 0.0 to 3.0, preferably from 0.0 to 2.2, e.g., from 0.0 to 2.0, and an average carbon number ("ACN") ranging from 9.0 to 9.4 are useful as low viscosity plasticizers.

More particularly, it has been determined that mixtures of one or more compounds of the general formula:

wherein R is an alkyl residue of an alcohol having a degree of branching ranging from 0.0 to 3.0, preferably from 0.0 to 2.2, e.g., from 0.0 to 2.0, and an ACN ranging from 9.0 to 9.4 are especially useful low viscosity plasticizers. In one embodiment, different alcohols that have a carbon number ranging from 8 to 11 ($C_8$ to $C_{11}$), preferably from 9 to 10 ($C_9$ to $C_{10}$) are employed to make the esters in the mixture. In a preferred embodiment, different nonyl alcohols are employed to make the ester. In another embodiment only one nonyl alcohol is employed to make the esters in the mixture.

For purposes of this specification, the term "average carbon number" means the average of individual molecule carbon numbers in a group of one or more molecules. The ACN of the alcohols is determined by $^1$H NMR spectroscopy.

"Hydroformylating" or "hydroformylation" is the process of reacting a compound having at least one carbon-carbon double bond (an olefin) in an atmosphere of carbon monoxide and hydrogen over a cobalt or rhodium catalyst, which results in addition of at least one aldehyde moiety to the underlying compound. U.S. Pat. No. 6,482,972, which is incorporated herein by reference in its entirety, describes the hydroformylation (OXO) process.

"Hydrogenating" or "hydrogenation" is addition of hydrogen ($H_2$) to a double-bonded functional site of a molecule, such as saturation of the double bonds in an aromatic ring.

A "plastisol" is a fluid or a paste consisting of a mixture of emulsion polyvinyl chloride and a plasticizer, and optionally containing various additives.

Suitable methyl biphenyl carboxylic acid esters and their method of production are described in US 2015/0140350, which is fully incorporated herein by reference.

Low viscosity plasticizers are particularly useful for PVC plastisols where they reduce the initial plastisol viscosity as well as the plastisol viscosity under shear stress. It has been found that the performance properties of the methyl biphenyl carboxylic acid esters can be tailored by selecting the appropriate methyl biphenyl carboxylic acid ester isomer structure(s) and the appropriate alcohol or alcohol mixture for producing the residue alkyl moiety(s) in the esters.

Methyl Biphenyl Carboxylic Acid Ester Isomers

The inventive mixture can be made of one or more isomers of the methyl biphenyl carboxylic acid esters written generically n'-methyl biphenyl-n-carboxylic acid esters. The position numbering (n' and n) for substituents on biphenyl is as indicated in following formula:

Suitable isomers of the methyl biphenyl carboxylic acid esters useful in the inventive ester mixtures include 4'-methylbiphenyl-4-carboxylic acid ester ("4'-4" or "para-para"), 4'-methylbiphenyl-3-carboxylic acid ester ("4'-3" or "para-meta"), 4'-methylbiphenyl-2-carboxylic acid ester ("4'-2" or "para-ortho") respectively represented by the formulas:

wherein R is an alkyl, preferably an alkyl residue of an alcohol.

Suitable isomers of the methyl biphenyl carboxylic acid esters useful in the inventive ester mixtures also include 3'-methylbiphenyl-4-carboxylic acid ester ("3'-4" or "meta-para"), 3'-methylbiphenyl-3-carboxylic acid ester ("3'-3" or "meta-meta"), 3'-methylbiphenyl-2-carboxylic acid ester ("3'-2" or "meta-ortho") respectively represented by the formulas:

-continued wherein R is an alkyl, preferably an alkyl residue of an alcohol.

Suitable isomers of the methyl biphenyl carboxylic acid useful in the inventive ester mixtures also include 2'-methylbiphenyl-4-carboxylic acid ester ("2'-4" or "ortho-para"), 2'-methylbiphenyl-3-carboxylic acid ester ("2'-3" or "ortho-meta"), 2'-methylbiphenyl-2-carboxylic acid ester ("2'-2" or "ortho-ortho") respectively represented by the formulas:

wherein R is an alkyl, preferably an alkyl residue of an alcohol.

It has been observed that methyl biphenyl carboxylic acid ester isomers having the methyl and carboxylic acid ester substituents closer to the para positions have lower viscosity than other isomers of the same ester. The para-para (4'-4) isomer of methyl biphenyl carboxylic acid ester has a lower viscosity than the para-meta (4'-3) or meta-para (3'-4) isomers of the same ester. Additionally, the para-meta (4'-3) and meta-para (3'-4) isomers of methyl biphenyl carboxylic acid ester have lower viscosity than the meta-meta (3'-3) isomers of the same ester. The meta-meta (3'-3) isomer of methyl biphenyl carboxylic acid ester has lower viscosity than the meta-ortho (3'-2), ortho-meta (2'-3), and ortho-ortho (2'-2) isomers of the same ester.

Preferably, the methyl biphenyl carboxylic acid ester(s) isomers in the inventive mixtures are para-para (4'-4), para-meta (4'-3), meta-para (3'-4), and meta-meta (3'-3) isomers. More preferably, the methyl biphenyl carboxylic acid ester(s) isomers in the inventive mixtures are para-para (4'-4), para-meta (4'-3), and meta-para (3'-4) isomers. Even more preferably, the methyl biphenyl carboxylic acid ester(s) isomers in the inventive mixtures are the para-para (4'-4) isomers.

It has been observed that carboxylic acid ester substituent position in the methyl biphenyl carboxylic acid ester has a stronger influence on viscosity of the ester than does the methyl substituent. The meta-para (3'-4) isomer of methyl biphenyl carboxylic acid ester has lower viscosity than the para-meta (4'-3) isomer of the same ester. Likewise, the ortho-meta (2'-3) isomer of methyl biphenyl carboxylic acid ester has lower viscosity than the meta-ortho (3'-2) isomer of the same ester.

Preferably, isomers have the carboxylic acid ester substituent located in the para or meta position. More preferably, the isomers have the carboxylic acid ester substituent located in the para position.

Preferably, the methyl biphenyl carboxylic acid ester(s) isomers in the inventive mixtures are para-para (4'-4), meta-para (3'-4), para-meta (4'-3), and meta-meta (3'-3) isomers. More preferably, the methyl biphenyl carboxylic acid ester (s) isomers in the inventive mixtures are para-para (4'-4), meta-para (3'-4), and para-meta (4'-3) isomers. Even more preferably, the methyl biphenyl carboxylic acid ester(s) isomers in the inventive mixtures are para-para (4'-4) and meta-para (3'-4) isomers.

Advantageously, the viscosity of the inventive methyl biphenyl carboxylic acid ester mixtures can be tailored by increasing or decreasing the concentration of isomers having substituents in the para-para, meta-para, para-meta, and/or meta-meta positions according to the above observations. One non-limiting example application is increasing the concentration of para-para (4'-4) isomers to lower the viscosity of a mixture of meta-meta (3'-3) and para-meta (4'-3) isomers of methyl biphenyl carboxylic esters. Various other applications will be understood by one having ordinary skill in the art.

It has been further observed that para-para (4'-4) isomers of methyl biphenyl carboxylic acid esters, particularly esters of more linear alcohols, tend to form undesirable solids. Without being limited by any theory, it is believed that the structure afforded by the (4'-4) isomer and the more linear alcohols contributes to the ester forming a solid. However, it has been found that mixing para-para (4'-4) isomers with increasing amounts of the other isomers avoids the undesirable solid condition. Preferably, the inventive ester mixtures comprise ≤50 wt % para-para (4'-4) isomers.

In an embodiment of the invention, the mixture comprises from 20 to 50 wt % of para-para (4'-4) and/or meta-para (3'-4) isomers; from 50 to 80 wt % para-meta (4'-3) isomers; and ≤15 wt %, preferably ≤10 wt %, more preferably ≤5 wt % meta-meta (3'-3) isomers.

In another embodiment of the invention, the mixture comprises from 20 to 50 wt % of para-para (4'-4) isomers; from 50 to 80 wt % para-meta (4'-3) isomers and/or meta-para (3'-4); and ≤15 wt %, preferably ≤10 wt %, more preferably ≤5 wt % meta-meta (3'-3) isomers.

Alkyl Residuals of Alcohols

It has been found that methyl biphenyl carboxylic acid esters of the specified alcohols exhibit desirable low volatility comparable to diisononyl ortho-phthalate (DINP) or better than di-2ethyl hexyl phthalate (DEHP) but also very good gelation and fusion properties. More particularly, this improvement is exhibited in methyl biphenyl carboxylic acid esters made from a mixture of one or more alcohols wherein the ACN of the mixture is between 9.0 and 9.4 and the degree of branching in the alcohols is 3.0 or less, preferably 2.2 or less, e.g., 2.0 or less.

Accordingly, in any embodiment of the invention, the mixture comprises one or more compounds of the formula indicated previously and copied here for convenient reference:

where R is an alkyl residue of an alcohol (e.g., a nonyl alcohol).

When an ester is formed from an alcohol, the alkyl residue retains the structure and structure related properties (e.g., ACN, branching index, etc.) of the alcohol other than removal of the OH⁻ group. The alcohols useful for forming the residue alkyls in the inventive methyl biphenyl carboxylic acid ester mixtures are primarily $C_9$ alcohols and have a degree of branching ranging from 0.0 to 3.0, preferably from 0.0 to 2.2, e.g., from 0.0 to 2.0, and an average carbon number ("ACN") ranging from 9.0 to 9.4. In one embodiment, the alcohols are all $C_9$ alcohols. The alcohols can be a single structure or they can be mixtures of alcohols. Any alcohols that have carbon number from 8 to 11 ($C_8$ to $C_{11}$), preferably from 9 to 10 ($C_9$ to $C_{10}$) can be used in such mixtures, so long as the mixture of alcohols has an ACN ranging from 9.0 to 9.4.

In any embodiment of the invention described herein, the alkyl residues are formed from alcohols and have an average carbon number of 9.0 to 9.4. In an embodiment, the alcohols have an average carbon number ranging from 9.0 to 9.4, including 9.00 to 9.25, 9.0 to 9.2, 9.00 to 9.15, 9.0 to 9.1, 9.05 to 9.40, 9.10 to 9.4, and 9.1 to 9.2. In an embodiment, the alcohol has an average carbon number of 9.00, 9.11, 9.01, 9.04, or 9.29.

Suitable alcohols are described in U.S. Pat. No. 8,329, 796; U.S. Pat. No. 7,786,201; and U.S. Pat. No. 6,437,170, which are fully incorporated herein by reference.

The nature and average carbon number of the alkyl residues present in the inventive esters can be determined by saponifying the ester in basic solution and then analyzing the resulting alcohols by $^1H$ NMR spectroscopy.

It has been found that viscosity of the methyl biphenyl carboxylic acid ester mixture can be reduced by increasing linearity (decreasing degree of branching) of the specified alcohol moiety(s). Suitable alcohol moieties have a degree of branching ranging from 0.0 to 3.0, including 0.0 to 2.2, 1.0 to 2.2, 1.0 to 2.0, 1.1 to 2.1, 1.1 to 2.0, 1.2 to 2.0, 1.2 to 1.9, 1.2 to 1.5, 1.3 to 1.8, and from 1.3 to 1.7, and any combination of the preceding ranges. Suitable alcohols used to form the alkyl residues in the ester mixture have a degree of branching ranging from 0.0 to 3.0, preferably 0.0 to 2.2, preferably 0.0 to 2.0, more preferably 0.0 to 1.5, even more preferably 0.0 to 1.0, still more preferably 0.0 to 0.5. In an embodiment of the invention, the alcohol used to form the alkyl residues in the ester mixture is n-nonanol.

$^1H$ NMR methods or $^{13}C$ NMR methods can be used to determine the degree of branching of the alcohol. According to the present invention, it is preferable to determine the degree of branching with the aid of $^1H$ NMR spectroscopy on a solution of the esters in deuterochloroform ($CDCl_3$). The spectra are recorded by way of example by dissolving 20 mg of substance in 0.6 ml of $CDCl_3$, comprising 1% by weight of tetramethylsilane (TMS), and charging the solution to an NMR tube with a diameter of 5 mm. Both the substance to be studied and the $CDCl_3$ used can first be dried over molecular sieve in order to exclude any errors in the values measured due to possible presence of water. The method of determination of the degree of branching is advantageous in comparison with other methods for the characterization of alcohol moieties, described by way of example in WO 03/029339, since water contamination in essence has no effect on the results measured and their evaluation. In principle, any commercially available NMR equipment can be used for the NMR-spectroscopic studies. The present NMR-spectroscopic studies used INOVA 500 equipment from Varian. The spectra were recorded at a temperature of 300 K using a delay of d1=10 seconds, 64 scans, a pulse length of 9.7 μs and a sweep width of 13 000 Hz, using a 5 mm BBO (broad band observer) probe head. The resonance signals are recorded in comparison with the chemical shifts of tetramethylsilane (TMS=0 ppm) as internal standard. Comparable results are obtained with other commercially available NMR equipment using the same operating parameters.

The degree of branching B can therefore be calculated from the measured intensity ratio in accordance with the following formula:

$$B = 2/3 * I(CH_3)/I(OCH_2) - 1$$

where B is degree of branching, $I(CH_3)$ is the area integral essentially attributed to the methyl hydrogen atoms, and $I(OCH_2)$ is the area integral for the methylene hydrogen atoms adjacent to the oxygen atom.

The ACN can therefore be calculated from the measured intensity ratio in accordance with the following formula:

$$ACN = I(CH_2, CH(OH) + I(CH_3)/I(OCH_2)$$

where ACN is the average carbon number, $I(CH_3)$ is the area integral essentially attributed to the methyl hydrogen atoms, and $I(OCH_2)$ is the area integral for the methylene hydrogen atoms adjacent to the oxygen atom.

The alcohols can generally be produced by hydroformylation of octenes, which in turn can be produced in various ways. The raw material generally used for the production of the octenes comprises industrial $C_4$ streams, which initially can comprise all of the isomeric $C_4$ olefins, alongside the saturated butanes and sometimes impurities such as $C_3$ and $C_5$ olefins and acetylenic compounds. Oligomerization of this olefin mixture gives mainly isomeric octene mixtures, alongside higher oligomers such as $C_{12}$ and $C_{16}$ olefin mixtures. These octene mixtures, from which the higher oligomers have preferably been removed by distillation, are hydroformylated to give the corresponding aldehydes, and then hydrogenated to give the alcohol. The constitution, i.e., the isomer distribution of these technical alcohol mixtures, depends on the starting material and on the oligomerization process and hydroformylation process.

Other examples of octene mixtures that can be used are those obtained by way of what is known as the polygas process, in which $C_3/C_4$ mixtures are oligomerized on a solid acidic catalyst, preferably on a solid phosphoric acid catalyst (SPA process). This process is described inter alia in the documents U.S. Pat. No. 6,284,938; U.S. Pat. No. 6,080, 903; U.S. Pat. No. 6,072,093; U.S. Pat. No. 6,025,533; U.S. Pat. No. 5,990,367; U.S. Pat. No. 5,895,830; U.S. Pat. No. 5,856,604; U.S. Pat. No. 5,847,252; and U.S. Pat. No. 5,081,086. The alcohols obtained by these processes generally also comprise octanols and decanols, and sometimes also undecanols, and the average chain length here can therefore deviate from 9 carbon atoms. This has no effect on the determination of the degree of branching B by the abovementioned method, however.

Because of the raw material used, and for process reasons, the constitution of this $C_9$-rich $C_8$-$C_{11}$ alcohol mixture is markedly more complex, and attribution of the individual peaks in the corresponding gas chromatograms cannot be achieved accurately without enormous additional cost. A characteristic of this nonyl-rich alcohol mixture is that the proportion of n-nonanol is generally markedly below two percent.

A distribution in typical alcohol mixture suitable for forming the alkyl residues of the inventive esters has from 2 to 3% of octanols, from 70 to 78% of nonanols, from 15 to 25% of decanols and at most 2% of undecanols. The boiling range (start of boiling to dry point) is from 202° C. to 219° C. at atmospheric pressure. Another alcohol mixture of this type, suitable for forming the alkyl residues in the inventive esters, is composed of from 5 to 10% by weight of methylethylhexanols, from 45 to 55% by weight of dimethylheptanols, from 5 to 20% by weight of methyloctanols, from 0 to 1% by weight of n-nonanol and from 15 to 25% of decanols. Non-limiting example mixtures of alcohols produced by this process that are suitable for forming the alkyl residues in the inventive esters have degree of branching from 1.4 to 2.2, in particular from 1.5 to 2.0, and particularly typically from 1.6 to 1.9.

Suitable alcohol mixtures can comprise isomeric nonanols obtainable via hydroformylation of a mixture of isomeric octenes and subsequent or simultaneous hydrogenation. The mixture of isomeric octenes here is obtained by bringing a hydrocarbon mixture comprising butenes into contact with an oligomerization catalyst, in particular with a catalyst comprising nickel oxide. The proportion of isobutene in the hydrocarbon mixture is preferably smaller than 20% by weight, preferably smaller than 10% by weight, particularly preferably smaller than 5% by weight, very particularly preferably smaller than 3% by weight, particularly preferably smaller than 1% by weight, preferably from 0.01 to 1% by weight and particularly preferably from 0.05 to 0.5% by weight, based on the butenes. The preparation of isomeric octenes via oligomerization of essentially linear butenes on supported nickel catalysts is known by way of example as the OCTOL process, which is described by way of example in EP 0 395 857 or EP 1 029 839.

The mixtures of isomeric octenes are then fed to a hydroformylation process. The hydroformylation process can take place in the presence of modified or unmodified cobalt catalysts or modified or unmodified rhodium catalysts. The hydroformylation process preferably takes place in the presence of unmodified cobalt compounds. The hydroformylation process is usually followed by a hydrogenation process. These hydroformylation/hydrogenation processes are known by way of example from EP 0 850 905 and EP 1 172 349. The hydroformylation process can also take place in the presence of rhodium catalysts. These hydroformylation processes are well known. Specific processes for hydroformylation which have particularly good suitability for production of mixtures which can be used in the inventive process and which comprise isomeric nonanols are described by way of example in WO 2004/020380. The processes described in those documents are carried out in the presence of cyclic carbonic esters.

It can also be advantageous, as described in EP 1 172 349, to begin by fractionating the mixture of isomeric octenes, prior to feeding to the hydroformylation process. This method can give octene fractions which have particularly good suitability for the production of mixtures which can be used in the inventive process and which comprise isomeric nonanols. The fractions can then be used in a relatively simple manner to obtain a mixture of isomeric octenes via mixing of suitable fractions, and this mixture is suitable for the production of mixtures of isomeric nonanols for use in the inventive process. Non-limiting example mixtures of suitable alcohols produced by this process have degree of branching from 1.1 to 1.4, in particular from 1.2 to 1.3.

Alternative variants from the OCTOL process that uses catalysts comprising nickel, by way of example, variants that instead use catalysts comprising Ti or comprising Zr, may be used for the production of the octene mixture. These alternative variants and in particular the catalysts are described by way of example in EP 1 171 413. Non-limiting example mixtures of suitable alcohols produced by this process have branching index from 1.0 to 1.4, in particular from 1.2 to 1.3.

The alcohols for forming alkyl residues in the inventive esters can also be OXO-alcohols.

"OXO-alcohols" are isomeric linear, branched, or mixtures of linear and branched, organic alcohols. "OXO-esters" are compounds having at least one functional ester moiety within its structure derived from esterification of a carboxylic acid portion or moiety of a compound with an OXO-alcohol.

OXO-alcohols can be prepared by hydroformylating olefins, followed by hydrogenation to form the alcohols. The resulting OXO-alcohols consist of multiple isomers of a given chain length due to the various isomeric olefins obtained in the oligomerization process, described below, in tandem with the multiple isomeric possibilities of the hydroformylation step.

Typically, the isomeric olefins are formed by light olefin oligomerization over heterogeneous acid catalysts, such as by propylene and/or butene oligomerization over solid phosphoric acid or zeolite catalysts. The light olefins are readily available from refinery processing operations. The reaction results in mixtures of longer-chain, branched olefins, which are subsequently formed into longer chain, branched alcohols, as described below and in U.S. Pat. No. 6,274,756, fully incorporated herein by reference in its entirety. Olefins for hydroformylation can also be prepared by dimerization of propylene or butenes through commercial processes such as the IFP Dimersol™ process or the Huls (Evonik) Octol™ process.

Branched aldehydes are then produced by hydroformylation of the isomeric olefins. The resulting branched aldehydes can then be recovered from the crude hydroformylation product stream by fractionation to remove unreacted olefins. These branched aldehydes can then be hydrogenated to form alcohols (OXO-alcohols). Single carbon number alcohols can be used in the esterification of the acids described above, or differing carbon numbers can be used to optimize product cost and performance requirements. The "OXO" technology provides cost advantaged alcohols.

The branched aldehydes can then be hydrogenated via the addition of hydrogen to the aldehyde moieties of the di-aldehyde to form the corresponding di-alcohol. Conditions for hydrogenation of an aldehyde are well-known in the art and include, but are not limited to temperatures of 0-300° C., pressures of 1-500 atmospheres, and the presence of homogeneous or heterogeneous hydrogenation catalysts such as, but not limited to Pt/C, Pt/Al$_2$O$_3$ or Pd/Al$_2$O$_3$ and Ni. Useful hydrogenation catalysts include platinum, palladium, ruthenium, nickel, zinc, tin, cobalt, or a combination of these metals, with palladium being particularly advantageous.

Alternatively, the OXO-alcohols can be prepared by aldol condensation of shorter-chain aldehydes to form longer chain aldehydes, as described in U.S. Pat. No. 6,274,756, followed by hydrogenation to form the OXO-alcohols.

The alcohols suitable for forming residue alkyls in the ester mixtures can comprise a mixture of isomerically pure nonanols and/or fractions of a plurality of isomeric nonanols. A large number of isomerically pure nonanols is commercially available. Nonanol mixtures or nonanol fractions are equally commercially available which do not have the properties preferred for the inventive process. Simple mixing of these isomerically pure nonanols with nonanol mixtures can produce mixtures of alcohols which have the desired degree of branching and which provide methyl biphenyl carboxylic acid ester mixtures with the properties demanded.

Commercially available suitable alcohol mixtures include, but are not limited to, EXXAL 9™ (ExxonMobil), EXXAL 9S™ (ExxonMobil), EXXAL 9YPF™ (ExxonMobil), Linevol 9™ (Shell), Isononanol (EVONIK), and Isononanol (INA) (BASF).

As discussed above, the alcohols can be used individually or together in alcohol mixtures having different chain lengths, or in isomeric mixtures of the same carbon chain length to make mixed esters for use as plasticizers. This mixing of carbon numbers and/or levels of branching can be advantageous to achieve the desired compatibility with PVC for the respective core alcohol or acid used for the polar moiety end of the plasticizer, and to meet other plasticizer performance properties.

Producing Methyl Biphenyl Carboxylic Acid Esters

One route to the esters of the present disclosure is by combination of two benzene molecules, by controlled hydrogenation, as follows:

According to this method, the cyclohexyl benzene so formed can be dehydrogenated to form biphenyl as follows:

The aromatic ring(s) are subsequently alkylated with an alcohol, such as methanol, which acts to add one or more methyl groups to the ring(s), followed by oxygenation of one of the pendant methyl group(s) to form a carboxylic acid group, and subsequently esterified with an alcohol or mixture of alcohols, ROH, to form methyl biphenyl carboxylic acid esters of the present disclosure, wherein ROH is an alcohol having a degree of branching ranging from 0.0 to 3.0, preferably from 0.0 to 2.2, e.g., from 0.0 to 2.0, and an average carbon number (ACN) ranging from 9.0 to 9.4.

Another route to plasticizers of the present disclosure is by oxidative coupling of two benzene molecules to form biphenyl, as follows: for benzene coupling: Ukhopadhyay, Sudip; Rothenberg, Gadi; Gitis, Diana; Sasson, Yoel. Casali Institute of Applied Chemistry, Hebrew University of Jerusalem, Israel. Journal of Organic Chemistry (2000), 65(10), pp. 3107-3110. Publisher: American Chemical Society, incorporated herein by reference.

Similarly to the first process, the biphenyl molecule is then alkylated, for example, with an alcohol, such as methanol, to add one or more methyl groups to the ring(s), followed by oxygenation of the pendant methyl group to form carboxylic acid group, and subsequently esterified with an alcohol, ROH, to form the esters of the present disclosure.

A similar process can be followed utilizing an alkyl aromatic, such as toluene as the starting material in place of benzene wherein ROH is an alcohol or mixture of alcohols having a degree of branching ranging from 0.0 to 3.0, preferably from 0.0 to 2.2, e.g., from 0.0 to 2.0, and an average carbon number (ACN) ranging from 9.0 to 9.4. Either monoesters or diesters can be formed, or both, depending on reaction conditions. The esters of the present disclosure are preferably monoesters for their substantially lower viscosity compared to diesters. Preferably, by appropriate control of the oxidation step so as to oxidize only one of the pendant methyl groups, monoester compounds of the following general formula can be formed:

wherein R is an alcohol or mixture of alcohols having a degree of branching ranging from 0.0 to 3.0, preferably from 0.0 to 2.2, e.g., from 0.0 to 2.0, and an average carbon number (ACN) ranging from 9.0 to 9.4.

"Esterifying" or "esterification" is reaction of a carboxylic acid moiety, such as an anhydride, with an organic alcohol moiety to form an ester linkage. Esterification conditions are well-known in the art and include, but are not limited to, temperatures of 0-300° C., and the presence or absence of homogeneous or heterogeneous esterification catalysts such as Lewis or Brønsted acid catalysts.

In a preferred embodiment, this invention relates to a process for making a mixture of methyl biphenyl carboxylic acid nonyl-esters of the general formula:

wherein R is an alkyl residual of an alcohol moiety having a degree of branching ranging from 0.0 to 3.0, preferably from 0.0 to 2.2, e.g., from 0.0 to 2.0, and an ACN ranging from 9.0 to 9.4, comprising the steps of: reacting benzene or alkylated benzene under conditions appropriate to form alkylated biphenyl; optionally alkylating biphenyl to form said alkylated biphenyl; oxidizing the alkyl group on said alkylated biphenyl to form one carboxylic acid group; and reacting said carboxylic acid group with alcohols under esterification conditions to form said mixture.

In a preferred embodiment of the invention, the reacting step is conducted with benzene, and said optional alkylating step is conducted with an alcohol (such as methanol).

In a preferred embodiment of the invention, the alkylating step is conducted in the presence of an acid catalyst.

In a preferred embodiment of the invention, the reacting step is conducted with benzene, further comprising the steps of: hydroalkylating benzene by reacting benzene in the presence of $H_2$ to hydrogenate one mole of said benzene to form cyclohexene, alkylating benzene with said cyclohexene to form cyclohexylbenzene; dehydrogenating said cyclohexylbenzene to form biphenyl; and alkylating one or both aromatic moieties of said biphenyl to form said alkylated biphenyl, where preferably the hydroalkylating step is conducted in the presence of a hydrogenation catalyst, the alkylating step is conducted with an alkylation catalyst, and the dehydrogenating step is conducted with a dehydrogenation catalyst.

In a preferred embodiment of the invention, the hydrogenation catalyst is selected from the group consisting of platinum, palladium, ruthenium, nickel, zinc, tin, cobalt, or a combination of these metals, with palladium being particularly advantageous; the alkylation catalyst is selected from the group consisting of zeolites, mixed metal oxides and the dehydrogenation catalyst is selected from the group consisting of platinum, pladium, Ru, Rh, nickel, zinc, tin, cobalt and combinations thereof.

In a preferred embodiment of the invention, the reacting step is conducted with benzene in the presence of oxygen and an oxidative coupling catalyst, forming biphenyl, further comprising the step of: alkylating one or both aromatic moieties of said biphenyl to form said alkylated biphenyl, wherein the alkylating step is preferably conducted with an alkylation catalyst.

In a preferred embodiment of the invention, the reacting step is conducted with toluene, further comprising the steps of: reacting toluene in the presence of $H_2$ and a hydrogenation catalyst to form methyl cyclohexene; reacting said methyl cyclohexene with toluene in the presence of an alkylation catalyst to form dimethyl cyclohexylbenzene; and dehydrogenating said dimethyl cyclohexylbenzene in the presence of a dehydrogenation catalyst to form the alkylated biphenyl, which is preferably dimethyl-biphenyl.

In a preferred embodiment of the invention, after reacting the acid group with an alcohol under esterification conditions, the reaction product is contacted with a basic solution such as saturated sodium bicarbonate or a caustic soda wash.

In a preferred embodiment of the invention, after reacting the acid group with an OXO-alcohol under esterification conditions, the reaction product is contacted with a basic solution such as saturated sodium bicarbonate or a caustic soda wash.

In a preferred embodiment of the invention, the crude ester is further stripped to remove excess alcohol and the stripped ester is treated with activated carbon to improve the liquid volume resistivity of the plasticizer.

In general, for a polymer resin to be plasticized, a plasticizer is required with a good balance of polarity or solubility (providing desired compatibility with the polymer resin) and also with low volatility and low viscosity. Higher viscosity plasticizers negatively affect processability and as such heating is required during mixing and formulation of the polymer and the plasticizer. A high plasticizer viscosity has similar effects on the processability of PVC plastisols containing the plasticizer.

Volatility is also an important factor which affects the ageing or durability of the plasticized polymer. Highly volatile plasticizers will diffuse and evaporate from the plastic resin matrix, thus losing mechanical strength in applications requiring long term stability/flexibility. Plasticizer loss from a resin matrix due to plasticizer volatility can be evaluated in accordance with ASTM D2288 by heating 10 g of plasticizer for 24 h at 155° C. and measuring the resulting weight loss.

It has been found that when alcohols having a degree of branching ranging from 0.0 to 3.0, preferably from 0.0 to 2.2, e.g., from 0.0 to 2.0, and an average carbon number (ACN) ranging from 9.0 to 9.4 are used as reactants for the esterification reactions described above, the resulting methyl biphenyl carboxylic acid esters are in the form of relatively high-boiling liquids (having low volatility better than DEHP and similar to DINP), which are readily incorporated into polymer formulations as plasticizers. Additionally, it has been found that the methyl biphenyl carboxylic acid esters based on such alcohols can have a viscosity ≤200 mPa·s, preferably ≤180 mPa·s, more preferably ≤150 mPa·s, even more preferably ≤120 mPa·s, still even more preferably ≤95 mPa·s, measured by Antoon Paar Viscosimeter at 20° C. in accordance with ASTM D445.

Surprisingly, the esters having alkyl residues of the alcohols specified herein also have lower glass transition temperature ($T_g$), higher thermal stability and are slightly faster gelling than esters made with other, non-specified alcohols. It has been found that when alcohols having a degree of branching ranging from 0.0 to 3.0, preferably from 0.0 to 2.2, e.g., from 0.0 to 2.0, and an average carbon number (ACN) ranging from 9.0 to 9.4 are used as reactants for the esterification reactions described above, the resulting esters have Tg of ≤−60° C., preferably ≤−62° C., more preferably ≤−64° C., even more preferably ≤−66° C.

The glass transition (Tg) is determined using Differential Scanning calorimetry (DSC). Typically, 5 to 10 mg of the neat plasticizer are sealed in an aluminium pan and loaded into the instrument at room temperature. The sample is preheated at 100° C. for 2 min, followed by cooling to −80° C. at a cooling rate of 10° C./min. The sample is maintained at −80° C. for two minutes, and then heated again at 10° C./min up to 50° C. The glass transition is recorded during this heating to 50° C.

Compositions Using the Esters

Any of the ester mixtures can be used as plasticizers for polymers, such as vinyl chloride resins, polyesters, polyurethanes, silylated polymers, polysulfides, acrylics, ethylene-vinyl acetate copolymer, rubbers, poly(meth)acrylics and combinations thereof, preferably polyvinylchloride.

In an embodiment, this invention relates to a polymer composition comprising a thermoplastic polymer and at least one plasticizer mixture of one or more methyl biphenyl carboxylic acid esters of alcohols having a degree of branching ranging from 0.0 to 3.0, preferably from 0.0 to 2.2, e.g., from 0.0 to 2.0, and an average carbon number ("ACN") ranging from 9.0 to 9.4.

In an embodiment, this invention relates to a polymer composition comprising a thermoplastic polymer and at least one plasticizer mixture of one or more compounds of the general formula:

wherein R is an alkyl residue of an alcohol having a degree of branching ranging from 0.0 to 3.0, preferably from 0.0 to 2.2, e.g., from 0.0 to 2.0, and a ACN ranging from 9.0 to 9.4.

Preferably the thermoplastic polymer is selected from the group consisting of vinyl chloride resins, polyesters, silyl-terminated polyethers, polyurethanes, ethylene-vinyl acetate copolymer, rubbers, poly(meth)acrylics and combinations thereof. Alternately, the polymer is selected from the group consisting of polyvinyl chloride (PVC), polyvinylidene chloride, a copolymer of polyvinyl chloride and polyvinylidene chloride, and polyalkyl methacrylate (PAMA). Preferably, the polymer is a copolymer of vinyl chloride with at least one monomer selected from the group consisting of vinylidene chloride, vinyl acetate, vinyl propionate, vinyl butyrate, vinyl benzoate, methyl acrylate, ethyl acrylate, and butyl acrylate.

In any embodiment of the invention, in the polymer composition comprising a thermoplastic polymer and one or more of the inventive methyl biphenyl carboxylic acid ester plasticizers, the amount of plasticizer is from 5 to 90 wt %, based upon the weight of the thermoplastic polymer and plasticizer, preferably from 10 to 100 wt %, even more preferably in the range from 15 to 90 wt %, even more preferably in the range from 20 to 80 wt %.

The polymer composition comprising a thermoplastic polymer and at least one inventive ester plasticizer described herein may optionally contain further additional plasticizers other than those produced herein, such as: dialkyl (ortho) phthalate, preferably having 4 to 13 carbon atoms in the alkyl chain; trialkyl trimellitates, preferably having 4 to 10 carbon atoms in the side chain; dialkyl adipates, having 4 to 13 carbon atoms; dialkyl sebacates preferably having 4 to 13 carbon atoms; dialkyl azelates preferably having 4 to 13 carbon atoms; preferably dialkyl terephthalates each preferably having 4 to 8 carbon atoms and more particularly 4 to 7 carbon atoms in the side chain; alkyl 1,2-cyclohexanedicarboxylates, alkyl 1,3-cyclohexanedicarboxylates and alkyl 1,4-cyclohexanedicarboxylates, and preferably alkyl 1,2-cyclohexanedicarboxylates each preferably having 4 to 13 carbon atoms in the side chain; dibenzoic esters of glycols; alkylsulfonic esters of phenol with preferably one alkyl radical containing 8 to 22 carbon atoms; polymeric plasticizers (based on polyester in particular), glyceryl esters, acetylated glycerol esters, epoxy estolide fatty acid alkyl esters, citric triesters having a free OH group or are acetylated with for example alkyl radicals of 4 to 9 carbon atoms, alkylpyrrolidone derivatives having alkyl radicals of 4 to 18 carbon atoms and also alkyl benzoates, preferably having 7 to 13 carbon atoms in the alkyl chain. In all instances, the alkyl radicals can be linear or branched and the same or different.

The polymer composition comprising a thermoplastic polymer and at least one plasticizer described herein prepared according to the present invention may further contain additives to optimize the chemical, mechanical or processing properties, said additives being more particularly selected from the group consisting of fillers, such as calcium carbonate, titanium dioxide or silica, pigments, thermal stabilizers, antioxidants, UV stabilizers, lubricating or slip agents, flame retardants, antistatic agents, biocides, impact modifiers, blowing agents, (polymeric) processing aids, viscosity depressants or regulators such as thickener and thinners, antifogging agents, optical brighteners, etc.

Thermal stabilizers useful herein include all customary polymer stabilizers, especially PVC stabilizers in solid or liquid form. Examples are those based on Ca/Zn, Ba/Zn, Pb, Sn, or on organic compounds (OBS), and also acid-binding phyllosilicates such as hydrotalcite. The polymer compositions to be used according to the present invention may have a thermal stabilizer content of 0.2 to 10, preferably 0.8 to 5 and more preferably 1.0 to 4 wt %, based upon the weight of the polymer composition.

It is likewise possible to use costabilizers with plasticizing effect in the polymer composition comprising a thermoplastic polymer and at least one plasticizer as described herein, in particular epoxidized vegetable oils, such as epoxidized linseed oil or epoxidized soya oil.

Antioxidants are also useful in the polymer composition comprising a thermoplastic polymer and at least one plasticizer described herein and can include sterically hindered amines—known as HALS stabilizers, sterically hindered phenols, such as Topanol™ CA, phosphites, UV absorbers, e.g., hydroxybenzophenones, hydroxyphenylbenzotriazoles and/or aromatic amines. Suitable antioxidants for use in the compositions of the present invention are also described for example in "Handbook of Vinyl Formulating" (editor: R. F. Grossman; J. Wiley & Sons; New Jersey (US) 2008). The level of antioxidants in the mixtures of the present invention is typically not more than 10 phr, preferably not more than 8 phr, more preferably not more than 6 phr and even more preferably between 0.01 and 5 phr (phr=parts per hundred parts of polymer composition).

Organic and inorganic pigments can be also used in the polymer composition comprising a thermoplastic polymer and at least one plasticizer as described herein. The level of pigments in the compositions to be used according to the present invention is typically not more than 10 phr, preferably in the range from 0.01 to 5 phr and more preferably in the range from 0.1 to 3 phr. Examples of useful inorganic pigments are $TiO_2$, CdS, $CoO/Al_2O_3$, and $Cr_2O_3$. Examples of useful organic pigments are for example azo dyes, phthalocyanine pigments, dioxazine pigments and also aniline pigments.

The polymer composition comprising a thermoplastic polymer and at least one plasticizer described herein may contain one or more filler, including mineral and/or synthetic and/or natural, organic and/or inorganic materials, for example, calcium oxide, magnesium oxide, calcium carbonate, barium sulphate, silicon dioxide, phyllosilicate, carbon black, bitumen, wood (e.g., pulverized, as pellets, micropellets, fibers, etc.), paper, natural and/or synthetic fibers, glass, etc.

The compositions described herein can be produced in various ways. In general, however, the composition is produced by intensively mixing all components in a suitable mixing container at elevated temperatures. The plastic pellet or powder (typically suspension PVC, microsuspension PVC or emulsion PVC) is typically mixed mechanically, i.e. for example in fluid mixers, turbomixers, trough mixers or belt screw mixers with the plasticizer and the other components at temperatures in the range from 60° C. to 140° C., preferably in the range from 80° C. to 100° C. The components may be added simultaneously or, preferably, in succession (see also E. J. Wickson "Handbook of PVC Formulating", John Wiley and Sons, 1993, pp. 747-ff). The polymer composition of PVC, plasticizer and other additive as described above (e.g., the PVC compound or the PVC paste) is subsequently sent to the appropriate thermoplastic moulding processes for producing the finished or semi-finished article, optionally a pelletizing step is interposed.

The polymer compositions (e.g., the PVC compound or the PVC paste) are particularly useful for production of garden hoses, pipes, and medical tubing, floor coverings, flooring tiles, underbody car coating and sealants, latex and caulk, films, sheeting, roofing, or roofing webs, pool liners, building protection foils, upholstery, and cable filling compound, sheathing and wire insulation, particularly wire and cable coating, coated textiles and wall coverings.

The plasticizers of the invention are useful across the range of plasticized polyvinyl chloride materials. The plasticizers of the invention are useful in the production of semi-rigid polyvinyl chloride compositions which typically contain from 10 to 40 phr, preferably 15 to 35 phr, more preferably 20 to 30 phr of plasticizer (phr=parts per hundred parts PVC); flexible polyvinyl chloride compositions which typically contain from 40 to 60 phr, preferably 44 to 56 phr, more preferably from 48 to 52 phr plasticizer; and highly flexible compositions which typically contain from 70 to 110 phr, preferably 80 to 100 phr, more preferably 90 to 100 phr of plasticizer.

One widespread use of polyvinyl chloride is as a plastisol. Useful plastisols may optionally contain various additives, such as those described above. A plastisol is used to produce one or more layers of polyvinyl chloride which are coated, pre-gelled, literally built-up and fused to produce coherent articles of flexible polyvinyl chloride. Plastisols are useful in the production of flooring, tents, tarpaulins, coated fabrics such as automobile upholstery, in car underbody coatings, in mouldings and other consumer products. Plastisols are also used in footwear, fabric coating, toys, vinyl gloves, and wallpaper. Plastisols typically contain 40 to 200 phr, more typically 50 to 150 phr, more typically 70 to 120 phr, more typically 90 to 110 phr of plasticizer.

In a preferred embodiment of the invention, one or more (such as two or three) plasticizers produced herein are combined with a polymer such as PVC to form a PVC compound (typically made from suspension PVC) or a PVC paste (typically made from an emulsion PVC). A particularly useful PVC in the PVC compound or paste is one having a K value from 60 to 90, preferably above 70, more preferably from 70 to 85. Particularly preferred PVC compounds or paste comprise: 20 to 150 phr (parts per hundred of resin) plasticizer(s), more preferably 30 to 70 phr and/or 0.5 to 15 phr stabilizer(s), and/or 1 to 30 phr, preferably 15 to 30 phr, filler(s), even more preferably the filler is calcium carbonate and the stabilizer is a calcium/zinc stabilizer. The above combination is useful in wire and cable coatings, particularly automobile wire and cable coating and or building wire insulation.

EXAMPLES

The following examples are meant to illustrate the present disclosure and inventive processes, and provide where appropriate a comparison with other methods, including the products produced thereby. Numerous modifications and variations are possible and it is to be understood that within the scope of the appended claims, the disclosure can be practiced otherwise than as specifically described herein.

Branching and carbon number distribution (ACN) characteristics of alcohols suitable for forming the alkyl residue in the inventive esters are provided in Table 1, below.

TABLE 1

Branching (B) and Average Carbon Number (ACN) of Suitable Alcohols

|   | n-Nonanol | A1 | A2 | A3 | A4 | A5 | A6 | A7 | Nonanol 3,5,5 Trimethyl Hexanol |
|---|---|---|---|---|---|---|---|---|---|
| B | 0.0 | 0.13 | 0.33 | 1.26 | 1.4 | 1.36 | 1.9 | 1.91-2.06 | 3.0 |
| ACN | 9.0 | 9.11 | 9.11 | 9.01 | 9.12 | 9.04 | 9.01 | 9.29-9.37 | 9.0 |

Commercially available alcohols:
A1 is Linevol 9 from Shell;
A2 is ExxonMobil linear $C_9$ alcohol;
A3 is INA from Oxeno;
A4 is INA from BASF;
A5 is ExxonMobil Exxal™ 9 YPF;
A6 is ExxonMobil Exxal™ 9S; and
A7 is ExxonMobil Exxal™ 9.

Viscosity characteristics, measured at 20° C. using Antoon Paar viscometer in accordance with ASTM D445, of example methyl biphenyl carboxylic acid esters of selected alcohols described in Table 1 and prepared by methods described above are provided in Table 2, below.

TABLE 2

Viscosity for Methyl Biphenyl Carboxylic Acid Ester Isomers (mPa · s at 20° C.)

| Ester Isomer | n-nonanol | A2 | A3 | A7 |
|---|---|---|---|---|
| 3'-3 | 100 | 120 | 192 | 233 |
| 3'-4 |  |  |  | 184 |
| 4'-4 | Likely Solid* |  |  | 151 |

*Not measured - prophetic

Figure 1:
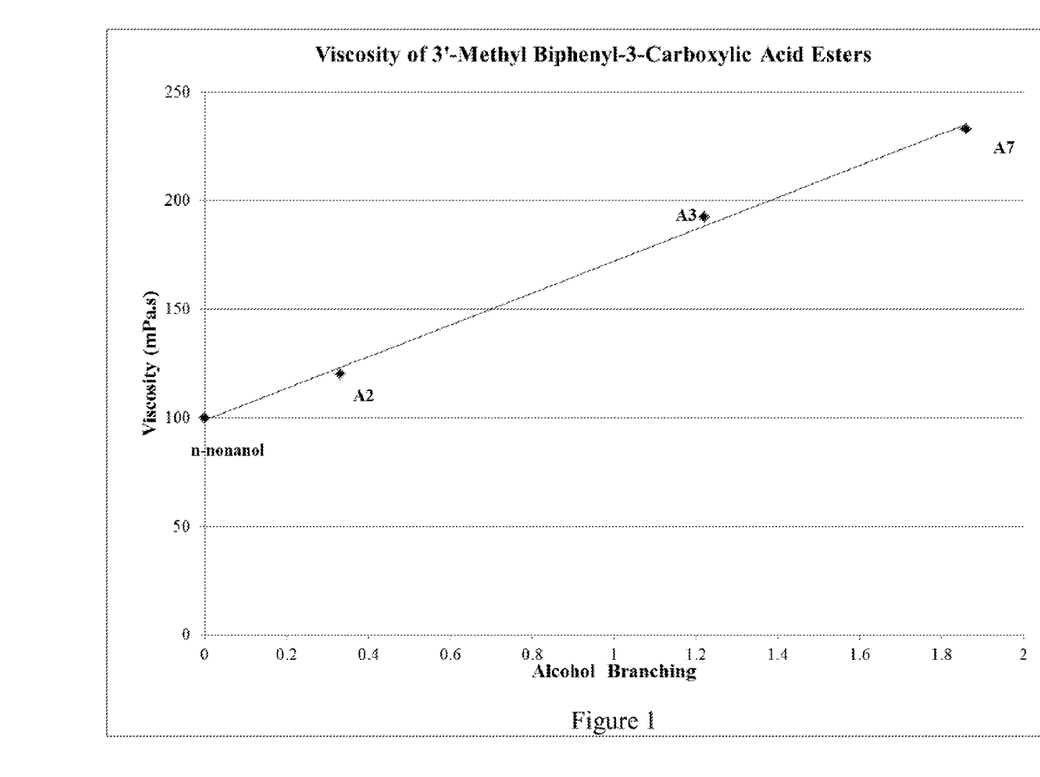
FIG. 1 shows viscosity of methyl biphenyl carboxylic acid esters.

The methyl biphenyl carboxylic acid ester examples in Table 2 clearly indicate the impact of the degree of branching of the alkyl moiety on the resulting ester viscosity, esters of the straight chain n-nonanol demonstrating the lowest viscosity. The magnitude of the viscosity decrease was particularly surprising when going from branched to linear alcohol esters. The 3'-3 isomer of the methyl biphenyl carboxylic acid esters of alcohols A7 (branching index of 1.91) had a viscosity of 233 mPa·s, whereas the same isomer of esters from linear n-nonanol (branching index of 0.0) had a viscosity of only 100 mPa·s, less than half the viscosity of the branched esters. FIG. 1 further illustrates this surprising decrease in viscosity with decreased alcohol branching.

Referring again to Table 1, the viscosity of A7 based methyl biphenyl carboxylic acid esters decreased from 233 mPa·s for the meta-meta (3'-3) isomers to 151 mPa·s for the para-para (4'-4) isomers. The limit to this advantageous effect as discussed above is the linear 4'-4 isomer esters. The viscosity of these esters was not measured because they are expected to be solid, having a pour point above 20° C. Further support for this prophetic estimation of pour point may be found in discussion of Table 3.

Table 3 contains viscosity and pour point measurements for methyl biphenyl carboxylic acid example esters of alcohols (A7) and comparative examples using $C_7$ or $C_4$ branched or linear alcohols. In particular, comparative examples comprised methyl carboxylic acid esters of n-heptanol, n-butanol, and of a primarily $C_7$ branched alcohol mixture. The para-para (4'-4) isomer esters of linear n-heptanol and n-butanol were solid at 20° C. preventing measurement of their viscosity. However, the meta-para (3'-4) isomer esters of the linear alcohols were liquid at 20° C. enabling a viscosity measurement to be obtained. Particularly interesting, a mixture of a solid ester of 4'-4 isomer made with n-heptanol and a liquid ester of 3'-4 isomer made with n-heptanol is liquid in a ratio 75 wt % 3'-4 isomer to 25 wt % 4'-4 isomer (75/25) and 65 wt % 3'-4 isomer to 35 wt % 4'-4 isomer (65/35). Additionally, the pour point of the 65/35 isomer mixtures for all alcohols is well below room temperature.

TABLE 3

Viscosity (mPa · s at 20° C.) and Pour Point (° C.) for Methyl Biphenyl Carboxylic Acid Ester Isomer Mixtures

| | 3'-4 Isomer | 4'-4 Isomer | 75/25 ratio | 65/35 ratio | Pour Point (° C.) of the 65/35 |
|---|---|---|---|---|---|
| A7 | 184 | 151 | 181 | 178 | −38 |
| Branched $C_7$ Alcohol Mix | 128 | 98 | 127 | 118 | −40 |
| n-heptanol | 85 | Solid | 80 | 79 | −44 |
| n-butanol | 70 | Solid | 65 | 63 | −43 |

(Pour point measured in accordance with ASTM D5950. Viscosity was measured at 20° C. using Antoon Paar viscometer in accordance with ASTM D445)

The viscosity of methyl biphenyl carboxylic acid esters isomer mixtures of A7 alcohols is illustrated in Table 3. The 65/35 isomer mix of A7 esters had lower viscosity (178 mPa·s) than the 3'-4 isomers (184 mPa·s).

Table 4 below illustrates the viscosity for methyl biphenyl carboxylic acid ester mixtures of alcohols. As seen below, a mixture ratio of 75 wt % n-nonanol based 3'-3 ester to 25 wt % A7 based ester (75/25) had a desirable viscosity of 121 mPa·s and a mixture ratio of 75 wt % A2 based ester to 25 wt % A7 based ester (75/25) had a viscosity of 141 mPa·s.

TABLE 4

Viscosity (mPa · s at 20° C.) of Methyl Biphenyl Carboxylic Acid Esters of Alcohol Mixtures

| Ester Isomers | n-nonanol | A7 | Ratio 75/25 | Ratio 50/50 |
|---|---|---|---|---|
| 3'-3 | 100 | 233 | 121 | 162 |
| | A2 | A7 | Ratio 75/25 | Ratio 50/50 |
| 3'-3 | 120 | 233 | 141 | 179 |

(Viscosity was measured at 20° C. using Antoon Paar viscometer in accordance with ASTM D445)

Glass transition temperature characteristics of example methyl biphenyl carboxylic acid esters prepared by methods described above are provided in Table 5 below. The glass transition (Tg) was determined using Differential Scanning calorimetry (DSC) as described previously. The results in table 5 show that the glass transition is decreasing with the increasing linearity of the alkyl moiety. Plasticizers exhibiting a lower Tg will result in better cold flexibility properties when mixed with PVC.

TABLE 5

Glass Transition (Tg) for Methyl Biphenyl Carboxylic Acid Ester Isomers (° C.)

| Isomer | n-nonanol | A2 | A3 | A7 |
|---|---|---|---|---|
| 3'-3 | −70.9 | −69.6 | −66.9 | −62.8 |
| 3'-4 | | | | −61.7 |
| 4'-4 | Likely Solid* | | | 10.6 |

*Not measured - prophetic

Table 6 contains volatility measurements for comparative phthalate plasticizers and example inventive methyl biphenyl carboxylic acid esters of alcohols A2 and n-nonanol. Volatility was measured by Thermogravimetic analysis and was conducted on the neat plasticizers using a TA Instrument Q500 instrument (25-400° C., 10° C./min under Argon). The results show that esters of the present invention exhibit lower weight loss at 220° C. than comparative DINP ($C_9$ ortho phthalates) or DOTP ($C_8$ tere phthalates).

TABLE 6

Thermogravimetic Analysis (TGA)

| | Temperature at 1% weight loss (° C.) | Temperature at 5% weight loss (° C.) | Temperature at 10% weight loss (° C.) | Weight Loss at 220° C. |
|---|---|---|---|---|
| DINP | 197 | 229.6 | 245.6 | 3.2 |
| DOTP | 198 | 232 | 248 | 2.9 |
| 3'-3 n-nonanol | 200 | 233 | 249 | 2.7 |
| 3'-3 A2 | 197 | 233 | 249 | 2.8 |

Table 7 below contains comparative and example PVC plastisol compositions and Brookfield viscosity data. PVC plastisols were prepared by mixing in a Hobart mixer. The plastisols were prepared with 100 parts per hundred of PVC, 40 parts of plasticizer, and 2 parts of a conventional CaZn stabilizer. The plastisol viscosity was determined by rotational Brookfield viscometer, equipped with standard disc spindles (RV series). Example formulations T48 (containing inventive ester of n-nonanol) and T49 (containing inventive ester of A2 alcohol) exhibited a similar viscosity to formulation T48 (DINP). The below data demonstrate that inventive plastisols based on n-nonanol ester exhibit lower initial viscosity compared to a higher branched $C_9$ alcohol ester.

TABLE 7

Example of plastisol formulations (vinyl flooring top layer)

| | Formulations (parts per hundred) | | | |
|---|---|---|---|---|
| | T46 | T9 | T48 | T49 |
| Solvin 382 NG | 80 | 80 | 80 | 80 |
| Solvin 266 SF | 20 | 20 | 20 | 20 |
| Jayflex DINP | 40 | | | |
| 3'-4/4'-4 Isononanol 65/35 | | 40 | | |
| 3'-3 n-nonanol | | | 40 | |
| 3'-3 A2 | | | | 40 |
| Lankromark LZC525 | 2 | 2 | 2 | 2 |
| Brookfield viscosity in (mPa · s) 2 hours | 9000 | High viscosity | 9000 | 11400 |

The gelation temperatures of the above plastisols were determined by an Antoon Paar Physica Rheometer MCR 301 and recorded in Table 8. The instrument was used in oscillation mode, frequency 1 hz, amplitude 0.01% and the heating rate is 10° C./min. The gelation is reported when G' (Elastic modulus) reaches $10^4$ Pa and $10^5$ Pa.

TABLE 8

| Plastisol Gelation (° C.) | | | | |
|---|---|---|---|---|
| | T46 | T9 | T48 | T49 |
| G' at $10^4$ Pa | 95 | 90.8 | 88.7 | 89.0 |
| G' at $10^5$ Pa | 106 | 93.8 | 93.0 | 93.2 |

Figure 2:
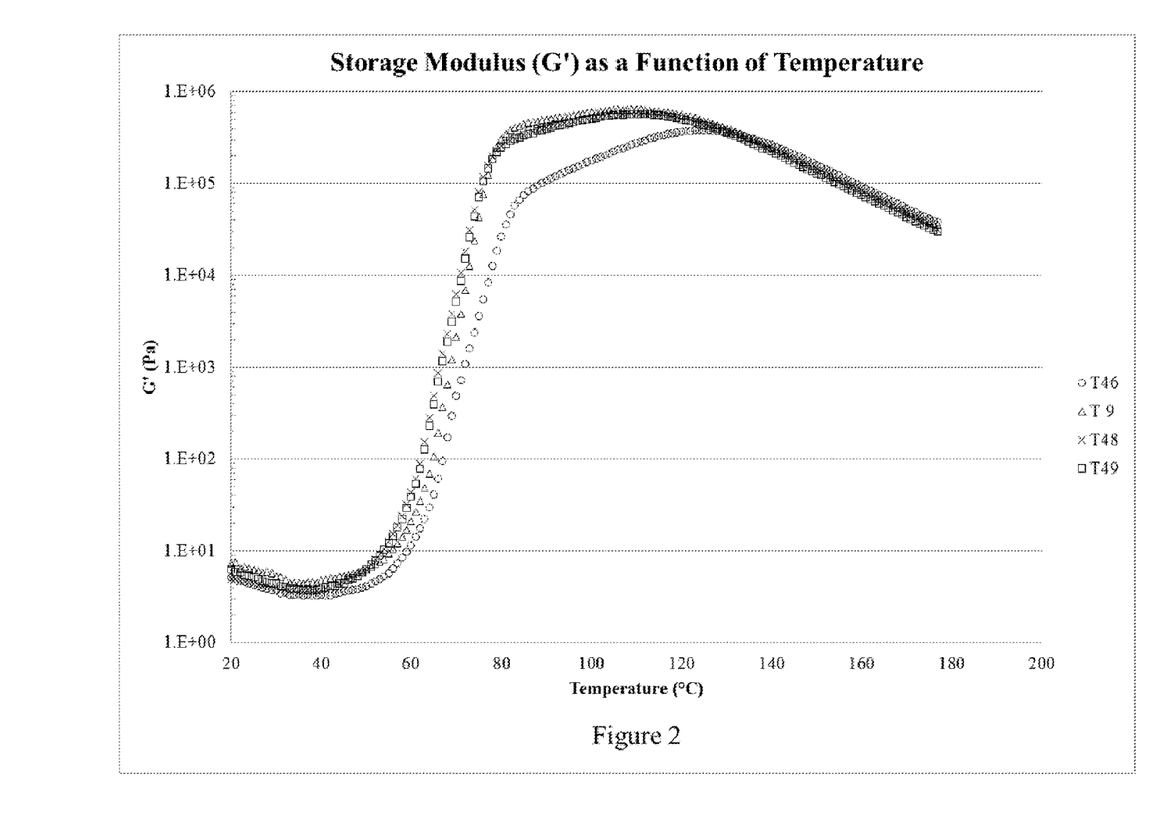
FIG. 2 shows the storage modulus (G') as a function of temperature for plastisol compositions obtained by dynamic mechanical analysis.

Formulations including the ester of the present invention are faster gelling than DINP as shown on the graph in FIG. 2 illustrating the gelation curves obtained by DMA (dynamic mechanical analysis) for each formulation.

The meanings of terms used herein shall take their ordinary meaning in the art; reference shall be taken, in particular, to Handbook of Petroleum Refining Processes, Third Edition, Robert A. Meyers, Editor, McGraw-Hill (2004). In addition, all patents and patent applications (including priority documents), test procedures (such as ASTM methods), and other documents cited herein are fully incorporated by reference to the extent such disclosure is not inconsistent with this disclosure and for all jurisdictions in which such incorporation is permitted. Also, when numerical lower limits and numerical upper limits are listed herein, ranges from any lower limit to any upper limit are contemplated. Note further that Trade Names used herein are indicated by a™ symbol, indicating that the names may be protected by certain trademark rights, e.g., they may be registered trademarks in various jurisdictions.

The disclosure has been described above with reference to numerous embodiments and specific examples. Many variations will suggest themselves to those skilled in this art in light of the above detailed description. All such obvious variations are within the full intended scope of the appended claims.

What is claimed is:

1. A plastisol comprising a thermoplastic polymer and at least one plasticizer mixture of one or more methyl biphenyl carboxylic acid esters of the following formula:

wherein R is an alkyl residue of n-nonanol having a degree of branching of 0.0 and a ACN of 9.0; and wherein the mixture of methyl biphenyl carboxylic acid esters comprise from 20 to 50 wt % of para-para from 50 to 80 wt % of para-meta (4'-3) isomers and/or meta-para (3'-4) isomers, and ≤15 wt % of meta-meta (3'-3) isomers.

2. The plastisol of claim 1, wherein the thermoplastic polymer is selected from the group consisting of vinyl chloride resins, polyesters, silyl-terminated polyethers, polyurethanes, ethylene-vinyl acetate copolymer, rubbers, poly(meth)acrylics and combinations thereof.

3. The plastisol of claim 1, wherein the thermoplastic polymer is selected from the group consisting of polyvinyl chloride (PVC), polyvinylidene chloride, a copolymer of polyvinyl chloride and polyvinylidene chloride, and polyalkyl methacrylate (PAMA).

4. The plastisol of claim 1, wherein the amount of plasticizer mixture is from 5 to 90 wt %, based upon the weight of the thermoplastic polymer and plasticizer mixture.

5. The plastisol of claim 1, further comprising at least one additional plasticizer.

* * * * *